(12) United States Patent
Tokuda et al.

(10) Patent No.: US 7,910,752 B2
(45) Date of Patent: Mar. 22, 2011

(54) ANTICANCER COMPOUND, INTERMEDIATE THEREFOR, AND PROCESSES FOR PRODUCING THESE

(75) Inventors: Harukuni Tokuda, Kyoto (JP); Katsumi Nishimura, Kochi (JP)

(73) Assignee: Taheebo Japan Co., Ltd., Osaka (JP)

( * ) Notice: Subject to any disclaimer, the term of this patent is extended or adjusted under 35 U.S.C. 154(b) by 835 days.

(21) Appl. No.: 11/885,216

(22) PCT Filed: Mar. 15, 2006

(86) PCT No.: PCT/JP2006/305111
§ 371 (c)(1),
(2), (4) Date: Aug. 28, 2007

(87) PCT Pub. No.: WO2006/098355
PCT Pub. Date: Sep. 21, 2006

(65) Prior Publication Data
US 2009/0042977 A1  Feb. 12, 2009

(30) Foreign Application Priority Data

Mar. 16, 2005 (JP) .................. 2005-075291
Jan. 10, 2006 (JP) .................. 2006-002482

(51) Int. Cl.
*C07D 307/92* (2006.01)
(52) U.S. Cl. ................................. 549/458
(58) Field of Classification Search .............. 549/458
See application file for complete search history.

(56) References Cited

U.S. PATENT DOCUMENTS

| | | | |
|---|---|---|---|
| 4,739,062 | A | 4/1988 | Bigi et al. |
| 5,663,197 | A | 9/1997 | Ueda et al. |
| 6,395,773 | B1 | 5/2002 | Hirai et al. |
| 2008/0300415 | A1 | 12/2008 | Iida et al. |

FOREIGN PATENT DOCUMENTS

| | | |
|---|---|---|
| JP | 63-196576 | 8/1988 |
| JP | 4-139177 | 5/1992 |
| JP | 9-235280 | 9/1997 |
| JP | 11-21284 | 1/1999 |
| JP | 2004-224802 | 8/2004 |
| JP | 3598168 | 9/2004 |

OTHER PUBLICATIONS

Hagiwara et al. "Domino Michael-O-alkylation reaction: one pot synthesis of 2, 4-diacylhydrofuran derivatives and its application to antitumor naphthofuran synthesis", *Journal of the Chemical Society, Perkin Transaction1*, 2001, vol. 22, pp. 2946-2957.

De Oliveira et al. "Synthesis of the naturally occurring naphto-[2,3-b]pyran-5, 10-quinones alpha caryopterone, dihydro-alpha-lapachone and 6-hydroxy-alpha-lapachone", *Tetrahedron Letters*, 1988, vol. 29, No. 2, pp. 155-158.

Ueda et al. "Production of anti-tumour-promoting furano-naphthaquinones in *Tabebuia Avellanedae* cell cultures". *Phytochemistry*, vol. 36, No. 2, pp. 323-325 (1994).

Chaker et al. "Studies on the oxidative additional of N, N-Dimethylamine to bromojuglones and bromomethyljuglones". *Chem. Pharm. Bull.*, vol. 42, No. 11, pp. 2238-2240 (1994).

O'Neil (Ed) et al. *The Merck Index*. Edition Thirteen, pp. 942-943 (2001).

Koyama et al., "Micellar Electrokinetic Chromatography (MEKC) Separation of Furanonapthoquinones from *Tabebuia impetiginosa*", Chemical & Pharmaceutical Bulletin, vol. 48, No. 6, 2000, pp. 873-875.

Fujimoto et al., "Studies on the structure and stereochemistry of cytotoxic furanonaphthoquinones from *Tabebuia impetiginosa*: 5- and 8-hydroxy-2-(1-hydroxyethyl)naphtho[2,3-b]furan-4,9-diones" Journal of the Chemical Society, Perkin Transactions 1: Organic and Bio-Organic Chemistry, vol. 10, 1991, pp. 2323-2327.

Oliveira et al., "Lignans and naphthoquinones from *Tabebuia incana*" Phytochemistry, vol. 34, No. 5, 1993, pp. 1409-1412.

Yamashita et al., "Stereoselective synthesis and cytotoxicity of a cancer chemopreventive naphthoquinone from *Tabebuia avellanedae*", Bioorganic & Medicinal Chemistry Letters, vol. 17, No. 23, 2007, pp. 6417-6420.

Evidence of "Exception to Lack of Novelty of Invention" submitted in Japanese patent Application No. 2007-145680 and English translation (Feb. 1, 2007).

*Primary Examiner* — Taofiq A Solola
(74) *Attorney, Agent, or Firm* — Hamre, Schumann, Mueller & Larson, P.C.

(57) ABSTRACT

The present invention provides a method for easily and inexpensively preparing a racemate or an optically-active 2-(1-hydroxyethyl)-5-hydroxynaphtho[2,3-b]furan-4,9-dione in high yields, 2-acetyl-2,3-dihydro-5-hydroxynaphtho[2,3-b]furan-4,9-dione which is useful as an intermediate for preparing NFD, and an anticancer agent comprising 2-(1-hydroxyethyl)-5-hydroxynaphtho[2,3-b]furan-4,9-dione as an active ingredient.

Said 2-(1-hydroxyethyl)-5-hydroxynaphtho[2,3-b]furan-4,9-dione is obtained in 4 or 5 steps by using comparatively inexpensive 5-hydroxynaphthalene-1,4-dione (also referred to as juglone) as a starting material.

20 Claims, No Drawings

ANTICANCER COMPOUND, INTERMEDIATE THEREFOR, AND PROCESSES FOR PRODUCING THESE

TECHNICAL FIELD

The present invention relates to 2-acetyl-2,3-dihydro-5-hydroxynaphtho[2,3-b]furan-4,9-dione and a preparation thereof, and a method for preparing anticancer active 2-(1-hydroxyethyl)-5-hydroxynaphtho[2,3-b]furan-4,9-dione from the said compound. The present invention also relates to an anticancer agent comprising a racemate or an α-isomer of 2-(1-hydroxyethyl)-5-hydroxynaphtho[2,3-b]furan-4,9-dione as an active ingredient.

BACKGROUND ART 2-(1-Hydroxyethyl)-5-hydroxynaphtho[2,3-b]furan-4,9-dione of the following formula:

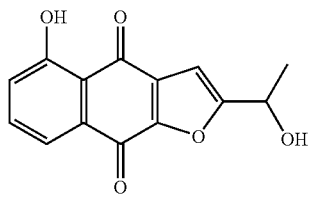

is an optically-active compound contained in Bignoniaceae, Taheebo (*Tabebuia avellanedae* Lorentz ex Griseb), which is β-isomer and is known to have an excellent anticancer activity (see, for example, Patent Document 1). However, a method for obtaining 2-(1-hydroxyethyl)-5-hydroxynaphtho[2,3-b]furan-4,9-dione is unknown except extraction from the said plant, and hence, 2-(1-hydroxyethyl)-5-hydroxynaphtho[2,3-b]furan-4,9-dione has not sufficiently been used as a medicine due to the rare availability of the plant and very low (0.05%) yields therefrom (see, for example, Nonpatent Document 1).

[Patent Document 1] JP2669762
[Nonpatent Document 1] Shinichi Ueda et al., Phytochemistry, 1994, Vol. 36(2), p. 323-325

DISCLOSURE OF INVENTION

Therefore, it is desirable to inexpensively and easily prepare 2-(1-hydroxyethyl)-5-hydroxynaphtho[2,3-b]furan-4,9-dione which is useful as a medicine.

Focusing that 5-hydroxynaphthalene-1,4-dione (also referred to as juglone) is available at a comparatively low cost, the present inventors have found that 2-(1-hydroxyethyl)-5-hydroxynaphtho[2,3-b]furan-4,9-dione can be inexpensively and easily synthesized in a high yield by using juglone as a starting material, and then have achieved the present invention. Thus, the present invention relates to a method for preparing 2-(1-hydroxyethyl)-5-hydroxynaphtho[2,3-b]furan-4,9-dione via an intermediate 2-acetyl-5-hydroxynaphtho[2,3-b]furan-4,9-dione which can be easily derived from juglone. The present inventors have achieved the present invention by recognizing that 2-(1-hydroxyethyl)-5-hydroxynaphtho[2,3-b]furan-4,9-dione prepared in this way can be obtained in a racemate form, and that the racemate can be separated into α- and β-isomers by an optical resolution in a conventional manner, and further, that the said racemate and α-isomer are safer than β-isomer.

The present invention provides a method for inexpensively and easily preparing 2-(1-hydroxyethyl)-5-hydroxynaphtho[2,3-b]furan-4,9-dione. Also, while 2-(1-hydroxyethyl)-5-hydroxynaphtho[2,3-b]furan-4,9-dione extracted from the plant is β-isomer, the method of the present invention can provide said compound in a racemic mixture. Further, it is possible to obtain an enantiomer of β-isomer (referred to as α-isomer hereinafter), which can not be obtained from the plant, by a chiral separation of the racemic mixture, for example a preparative isolation by a chiral column chromatography, or an optical resolution.

BEST MODE FOR CARRYING OUT THE INVENTION

In the first embodiment, the present invention provides a method for preparing a compound of the formula (III):

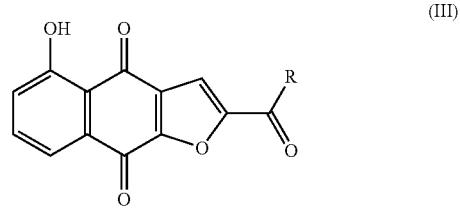

wherein R is $C_1$-$C_6$ alkyl, comprising reacting a compound of the formula (I):

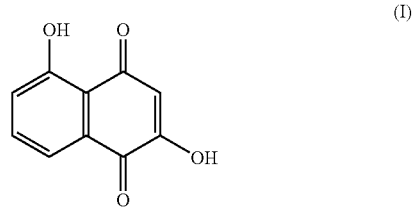

with a compound of the formula (II):

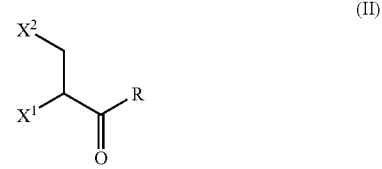

wherein R is the same as defined above and $X^1$ and $X^2$ are each independently halogen atom, in the presence of a base.

In a further embodiment, the present invention provides a method for preparing a compound of the formula (III):

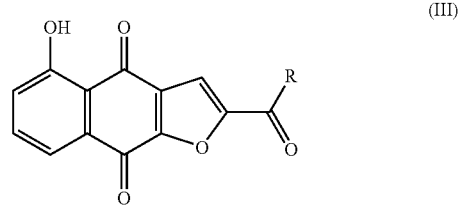

wherein R is $C_1$-$C_6$ alkyl, comprising reacting a compound of the formula (I):

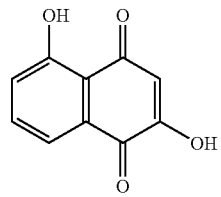

(I)

with a compound of the formula (II):

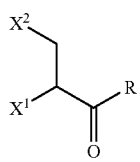

(II)

wherein R is the same as defined above and $X^1$ and $X^2$ are each independently halogen atom, in the presence of a base to give a compound of the formula (VII):

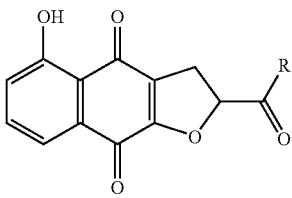

(VII)

wherein R is the same as defined above, followed by oxidizing the resulting compound (VII) by an oxidizing agent.

In a preferred embodiment, the present invention provides a method for preparation of a compound of the formula (IV):

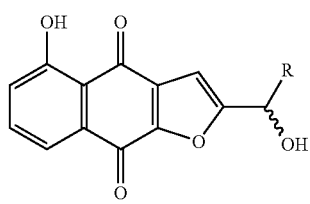

(IV)

wherein R is the same as defined above and a wavy line refers to a racemate, which further comprises a step of reducing a compound of the formula (III) obtained in any one of the above methods with a reducing agent.

Additionally, the present invention provides a method for preparing a racemic compound of the formula (IV):

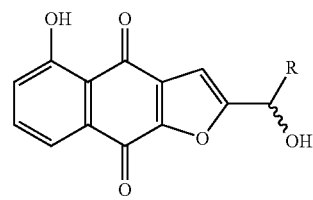

(IV)

wherein R is the same as defined above and a wavy line refers to a racemate, which comprises reducing a compound of the formula (III):

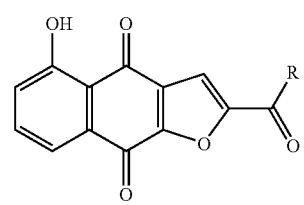

(III)

wherein R is the same as defined above, with a reducing agent, said compound (III) being prepared directly from a compound of the formula (I) or via a compound of the formula (VII).

In another embodiment, the present invention provides a method for preparing α- and β-isomers of 2-(1-hydroxyethyl)-5-hydroxynaphtho[2,3-b]furan-4,9-dione comprising resolving a compound of the formula (IV):

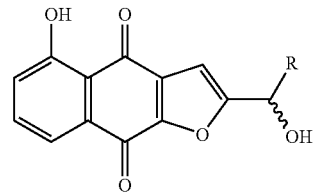

(IV)

wherein R is the same as defined above and a wavy line refers to a racemate.

In a further preferred embodiment, the present invention provides a method for preparation of various compounds as mentioned above, which comprises the steps of reacting a dimethylamine dissolved in a solvent with a compound of the formula (V):

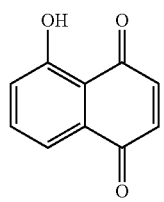

(V)

to give a compound of the formula (VI):

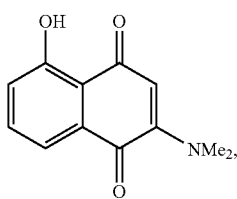

reacting the resulting compound of the formula (VI) with 5 to 15% by weight (w/w) of an aqueous acid solution to give a compound of the formula (I), and
comprising carrying out any one of the above-mentioned methods by using the resulting compound of the formula (I).

In another embodiment, the present invention provides a compound of the formula (VII):

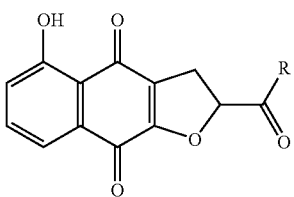

wherein R is the same as defined above. The said compound can be used as an intermediate for preparing 2-(1-hydroxyethyl)-5-hydroxynaphtho[2,3-b]furan-4,9-dione.

In a further embodiment, the present invention provides 2-(1-hydroxyethyl)-5-hydroxynaphtho[2,3-b]furan-4,9-dione having a (+)-optical rotation in methanol (c 0.25, 25° C.) referred to as α-isomer.

In another embodiment, the present invention provides an anticancer agent comprising a racemate of 2-(1-hydroxyethyl)-5-hydroxynaphtho[2,3-b]furan-4,9-dione as an active ingredient.

In another embodiment, the present invention provides an anticancer agent comprising an α-isomer of 2-(1-hydroxyethyl)-5-hydroxynaphtho[2,3-b]furan-4,9-dione as an active ingredient.

The term "oxidizing agent" used herein includes, without limiting, a manganese compound such as manganese dioxide or potassium permanganate, a chromium compound such as $CrO_3$ or $Na_2Cr_2O_7$, a lead compound such as PbO, $PbO_2$ or $Pb(OCOCH_3)_4$, other metal compounds such as HgO, AgO, $Ag_2O$, $AgNO_3$, $CuCl_2$ or $FeCl_3$, a halogen and halide compound such as $Cl_2$, $Br_2$, $I_2$, NaClO, $KBrO_3$ or $KIO4$, oxygen, ozone, peroxide such as $H_2O_2$, $Na_2O_2$ or $(C_6H_5CO)_2O_2$, or a peracid and a salt thereof such as $CH_3CO_3H$, $C_6H_5CO_3H$ or $K_2S_2O_8$.

The term "halogen" used herein includes fluorine, chlorine, bromine and iodine. Preferably, "halogen" is bromine.

The term "$C_1$-$C_6$ alkyl" used herein may be either straight- or branched-chain alkyl such as methyl, ethyl, n-propyl, isopropyl, n-butyl, tert-butyl, n-pentyl or n-hexyl. In the present invention, a preferable $C_1$-$C_6$ alkyl is methyl.

The term "base" used herein may be either an organic or an inorganic base. The organic base includes, for example, pyridine, DMAP (4-dimethylaminopyridine), quinoline, isoquinoline, triethylamine, diisopropylethylamine, DBU (1,8-diazabicyclo[5.4.0]undec-7-ene) or DBN (1,5-diazabicyclo[4.3.0]non-5-ene), but it is not limited thereto. The inorganic base includes hydroxide, carbonate, bicarbonate salt or the like of alkaline metal or alkali earth metal, such as sodium hydroxide, potassium hydroxide, calcium hydroxide, sodium carbonate or sodium bicarbonate, but it is not limited thereto. In the present invention, a preferable base is DBU.

The term "reducing agent" used herein includes, for example, sodium borohydride ($NaBH_4$), potassium borohydride, lithium borohydride, sodium aluminum hydride, potassium aluminum hydride, lithium aluminum hydride, zinc borohydride, sodium triacetoxyborohydride, pyridine/borane, sodium cyanoborohydride, sodium amalgam, $H_2$/Pd, $H_2$/Pd—C, $H_2$ IPt, $H_2$/$PtO_2$, $H_2$/Rh and $H_2$/Raney nickel, but it is not limited thereto. A preferable reducing agent is sodium borohydride.

The above obtained compound of the formula (VI) may be optionally separated by using a conventional method in the art, such as a fractional crystallization or a chiral column chromatography. Also, an optically active 2-(1-hydroxyethyl)-5-hydroxynaphtho[2,3-b]furan-4,9-dione may be obtained by a known method using a conventional chiral reducing agent instead of the above-mentioned reducing agent, said chiral reducing agent being, for example, a chiral borane derivative (e.g. (−)- or (+)-B-chlorodiisopinocampheylborane) or BINAP ((R)- or (S)-2,2'-bis(diphenylphosphino)-1,1'-binaphthyl)).

The method of the present invention can be illustrated as follows:

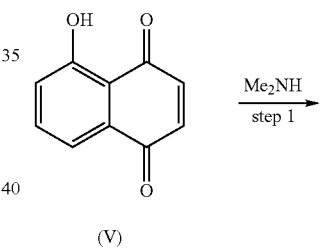

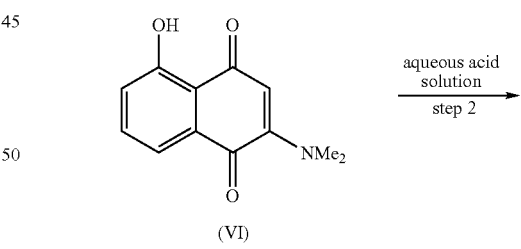

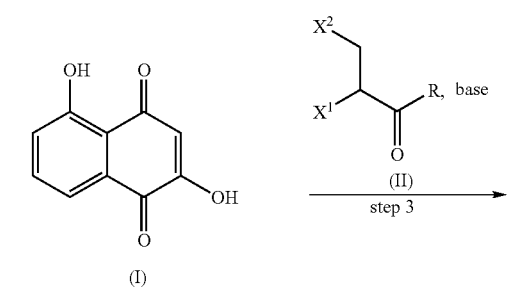

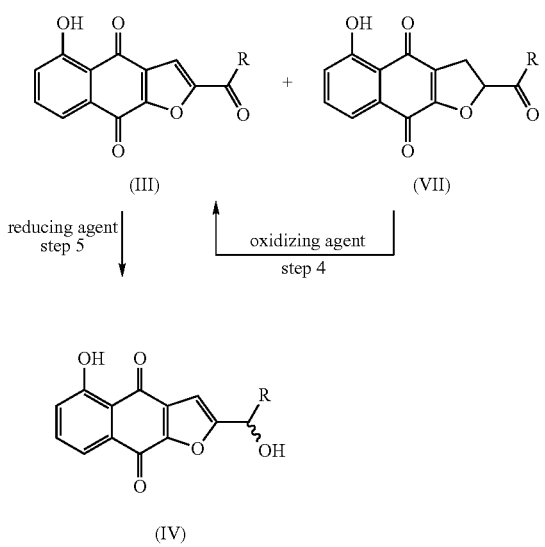

wherein R, $X^1$ and $X^2$ are the same as defined above.

The step 1 in the above scheme is preferably carried out according to the method described in Chaker, L.; Pautet, F.; Fillion, H., Chem. Pharm. Bull., 1994, 42, 2238-2240. Also, the starting material in step 1 of the above scheme 5-hydroxynaphthalene-1,4-dione (also referred to as juglone) is commercially available from, for example, Tokyo Chemical Industry Co., Ltd. (Tokyo, Japan). Further, juglone is described in detail in Merck Index, Edit. 13, p. 5288 and references therein.

The inventors have surprisingly found that in the method disclosed in the literature as mentioned above, even when a solution of dimethylamine in a solvent is used instead of dimethylamine (boiling point: −6° C.), similar results (substituent selectivities and yields) can be obtained. Accordingly, the present invention also provides a method of step 1 comprising adding a solution of dimethylamine in a solvent to a solution of juglone in toluene.

In step 1 of the above scheme, the solvent for juglone is not specified but includes any solvent usually used in the art. The preferred solvent is toluene. The solvent for dimethylamine is not specified either but includes any solvent usually used in the art. The preferred solvent includes water ($H_2O$), hexane, tetrahydrofuran (THF), diethyl ether, toluene, methanol and ethanol.

The reaction in step 1 may be carried out at a temperature in the range of −78° C. to a reflux temperature of a solvent, preferably from −40° C. to room temperature. Especially, a reaction temperature in the range of −40 to 0° C. is advantageous in terms of selectivities and ease of operations.

The reaction in step 2 of the above scheme may be preferably carried out according to a method described in De Oliveira, A.; Ferreira, D. T.; Raslan, D. S., Tetrahedron Lett., 1988, 29, 155-158.

The present inventors have surprisingly found that a concentrated hydrochloric acid used in the method of said literature may be replaced by 5 to 15% aqueous acid solution to achieve similar yields. The aqueous acid solution may be of any acid which can be generally used in a hydrolysis reaction, and preferred solution in an aqueous hydrochloric acid or sulfuric acid solution. Additionally, to the above aqueous solution dioxane may be optionally added dropwise. Also, the concentration of the acid are not specified but may be in any range as far as the hydrolysis can proceed, and it is preferably in the range of 5 to 15% in terms of safety and easy handling. Therefore, the present invention also provides a method of step 2 comprising using of 5 to 15% by weight of an aqueous acid solution, preferably 5 to 15% by weight of an aqueous hydrochloric acid solution. Also, the reaction in step 2 is carried out preferably under heating at reflux, while it is not specifically restricted.

The reaction in step 3 in the above scheme can be carried out in a similar manner as described in Hagiwara et al. (Hagiwara, H.; Sato, K.; Nishino, D.; Hoshi, T.; Suzuki, T.; Ando, M., J. Chem. Soc. Perkin Trans. 1, 2001, 2946-2957). While the yield of the product reported in the literature is 60%, substitution of 2-hydroxy juglone for the starting material described in the literature resulted in very low yield. According to the intensive study of the present inventors, it has been found that the reaction in step is much improved in yield by use of the reactant methyl vinyl ketone within 24 hours, preferably 3 hours, after distillation for purification. Therefore, the present invention also provides an improved method of step 3 by using methyl vinyl ketone immediately, preferably within one hour, after distillation for purification. In the step 3, a mixture of the compound (III) and the compound (VII) may be obtained. The compound (VII) may be changed to the compound (III) by treating with an oxidizing agent in the reaction in step 4.

The solvent for methyl vinyl ketone and bromine to be used in step 3 is not specified but is preferably pentane or hexane. On the other hand, the solvent for 2-hydroxy juglone is not specified but is preferably THF or diethyl ether. Additionally, a reaction temperature in step 3 is not specified but is preferably room temperature.

The reactions in steps 4 and 5 in the above scheme can be carried out by a method known in the art, preferably by the method described in Hagiwara et al. (Hagiwara, H.; Sato, K.; Nishino, D.; Hoshi, T.; Suzuki, T.; Ando, M., J. Chem. Soc. Perkin Trans. 1, 2001, 2946-2957).

Meanwhile, the reaction solvent in step 4 is not specified but is preferably hydrocarbon halide, for example chloroform or methylene chloride. Additionally, the reaction in step 4 is preferably carried out under heating with reflux, while it is not limited thereto.

The reaction solvent in step 5 is not specified but is preferably a mixture of chloroform and ethanol, particularly a mixture of chloroform:ethanol=4:1 (v/v). Additionally, the reaction in step 5 is preferably carried out at 0° C., while it is not limited thereto.

The present invention is illustrated by the following Examples, but is not intended to be limited to these Examples.

In the following Examples, the following instruments are used. 1H nuclear magnetic resonance spectrum ($^1$H-NMR): UNITY INOVA 500 (manufactured by Varian Inc.), Solvent for NMR: $CDCl_3$ (internal standard material: tetramethylsilane (TMS));

Apparatus for melting-point: Mp-J3 (Yanaco)

EXAMPLE 1

Preparation of 2-dimethylamino juglone

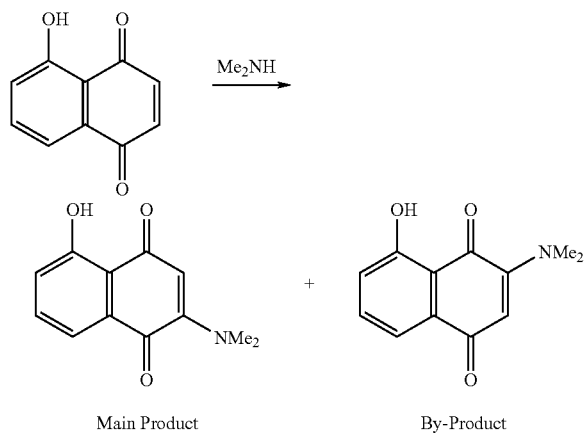

Main Product      By-Product

To a solution of 5-hydroxynaphthalene-1,4-dione (also referred to as juglone) (171 mg, 1 mmol) in toluene (5 mL) is added dimethylamine (0.75 mL, 2.0M solution in THF, 1.5 mmol) at −20° C. The mixture is stirred at −20° C. for 1 hour, then thereto is added dimethylamine (0.75 mL, 2.0M solution in THF, 1.5 mmol), and the mixture is stirred at −20° C. for additional 30 minutes, then the solvent is evaporated in vacuo. The residue is purified by silica gel column chromatography (chloroform/ethyl acetate=20/1 (v/v)) to isolate 2-dimethylamino juglone (87.2 mg, 40%) and 3-dimethylamino juglone (28.8 mg, 13%).

2-Dimethylamino juglone

Melting point: 147 to 148° C.

$^1$H-NMR (CDCl$_3$): δ 3.25 (s, 6H), 5.72 (s, 1H), 7.20 (dd, 1H, J=1.2, 8.3 Hz), 7.45-7.51 (m, 2H), 13.0 (s, 1H).

3-Dimethylamino juglone $^1$H-NMR (CDCl$_3$): δ 3.23 (s, 6H), 5.84 (s, 1H), 7.15 (dd, 1H, J=3.7, 6.1 Hz), 7.56-7.59 (m, 2H), 11.9 (s, 1H).

EXAMPLE 2

A reaction is carried out in the similar manner as described in Example 1, except substituting −40° C. for −20° C., to obtain 2-dimethylamino juglone (104 mg, 48%) and 3-dimethylamino juglone (20 mg, 10%).

EXAMPLE 3

A reaction is carried out in the similar manner as described in Example 1, except substituting water for THF for a solvent of dimethylamine, using 0.15 mL of an aqueous dimethylamine solution (50% aqueous solution, 1.5 mmol) and reacting at 0° C., to obtain 2-dimethylamino juglone (97 mg, 45%) and 3-dimethylamino juglone (67 mg, 31%). This method is more advantageous in environment and safety than the method of Example 1 in terms of substituting water for an organic solvent.

EXAMPLE 4

Preparation of 2-hydroxy juglone

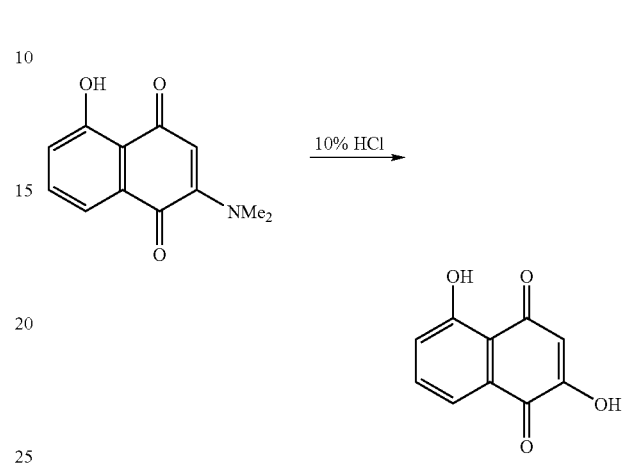

To a solution of 2-dimethylamino juglone (1.95 g, 9 mmol) in dioxane (45 mL) is added 10% hydrochloric acid (10 mL), and the mixture is heated to reflux for 30 minutes. The mixture is cooled to room temperature, and then the reaction solution is extracted with chloroform. The combined organic layers are washed with brine, dried over sodium sulfate, filtered, and the solvent is evaporated in vacuo to give 2-hydroxy juglone (1.67 g, 97%) as a brown solid.

Melting point: 220 to 221° C.

$^1$H-NMR (CDCl$_3$): δ 6.31 (1H, s), 7.35 (1H, dd, J=8.5, 1.2 Hz), 7.44 (1H, s), 7.59 (1H, t, J=8.5 Hz), 7.69 (1H, dd, J=8.5, 1.2 Hz), 12.33 (1H, s).

EXAMPLE 5

Preparation of 2-acetyl-5-hydroxynaphtho[2,3-b]furan-4,9-dione and 2-acetyl-2,3-dihydro-5-hydroxynaphtho[2,3-b]furan-4,9-dione

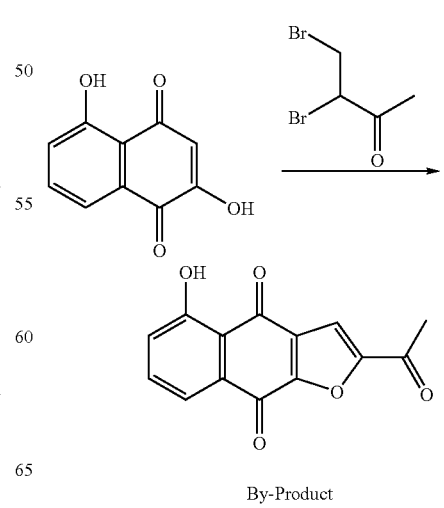

By-Product

-continued

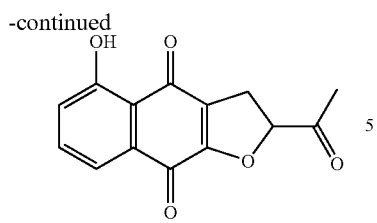

Main Product

To a solution of methyl vinyl ketone (10.5 g, 150 mmol) in pentane (150 mL) is added a solution of bromine (25 g, 156 mmol) in pentane (30 mL) at −15° C. The mixture is stirred at −15° C. for 10 minutes, and then the solvent is evaporated in vacuo to give a colorless oil. Then, the oil is added to a solution of 2-hydroxy juglone (4.75 g, 25 mmol) in THF (250 mL), and further DBU is added at 0° C., and the mixture is stirred at room temperature overnight. To the mixture is added 10% hydrochloric acid, and the reaction mixture is extracted with chloroform. The combined organic layers are washed with brine, dried over sodium sulfate, filtered, and the solvent is evaporated in vacuo. The residue is purified by silica gel column chromatography (eluent: chloroform/ethyl acetate=9/1 (v/v)) to give an orange solid mixture (6.14 g, 95%) comprising 2-acetyl-5-hydroxynaphtho[2,3-b]furan-4,9-dione and 2-acetyl-2,3-dihydro-5-hydroxynaphtho[2,3-b]furan-4,9-dione containing in the ratio of 1:5. This solid mixture is separated by silica gel column chromatography (eluent: chloroform) to give 2-acetyl-5-hydroxynaphtho[2,3-b]furan-4,9-dione and 2-acetyl-2,3-dihydro-5-hydroxynaphtho[2,3-b]furan-4,9-dione.

2-Acetyl-2,3-dihydro-5-hydroxynaphtho[2,3-b]furan-4,9-dione

Melting point: 175 to 182° C. (decomposition)
$^1$H-NMR (CDCl$_3$): δ 2.39 (3H, s), 3.39 (2H, d, J=9.5 Hz), 5.30 (1H, t, J=9.5 Hz), 7.26 (1H, dd, J=8.0, 1.0 Hz), 7.56 (1H, t, J=8.0 Hz), 7.65 (1H, dd, J=8.0, 1.0 Hz), 12.18 (1H, s).

2-Acetyl-5-hydroxynaphtho[2,3-b]furan-4,9-dione

Melting point: 208 to 220° C. (decomposition)
$^1$H-NMR (CDCl$_3$): δ 2.67 (3H, s), 7.33 (1H, dd, J=8.5, 1.0 Hz), 7.60 (1H, s), 7.67 (1H, t, J=8.3 Hz), 7.81 (1H, dd, J=7.4, 1.0 Hz), 12.13 (1H, s).

EXAMPLE 6

Preparation of 2-acetyl-5-hydroxynaphtho[2,3-b]furan-4,9-dione

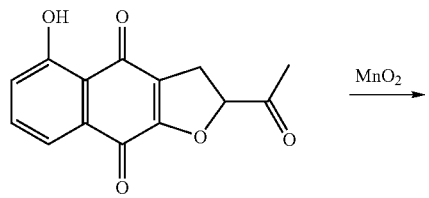

-continued

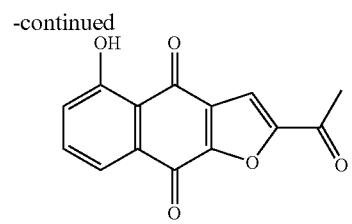

To a solution of 2-acetyl-2,3-dihydro-5-hydroxynaphtho[2,3-b]furan-4,9-dione (2.4 g, 9.4 mmol) in chloroform (50 mL) is added 20 g of manganese dioxide (manufactured by Aldrich Corp., 85% activated manganese dioxide, <5 micron), and the resulting suspension is heated to reflux for 1 day. The mixture is cooled to room temperature, and then filtered. The filtrate is evaporated in vacuo and the residue is purified by silica gel column chromatography (eluent: chloroform) to give 2-acetyl-5-hydroxynaphtho[2,3-b]furan-4,9-dione (0.718 g, 33%).

Melting point: 208 to 220° C. (decomposition)
$^1$H-NMR (CDCl$_3$): δ 2.67 (3H, s), 7.33 (1H, dd, J=8.5, 1.0 Hz), 7.60 (1H, s), 7.67 (1H, t, J=8.3 Hz), 7.81 (1H, dd, J=7.4, 1.0 Hz), 12.13 (1H, s).

Alternatively, in the above method of Example 6, manganese dioxide (manufactured by Aldrich Corp., 90% manganese dioxide, for battery cell, <10 micron) may be used instead of manganese dioxide (manufactured by Aldrich Corp., 85% activated manganese dioxide, <5 micron) (see the following Example 7).

EXAMPLE 7

To a solution of 2-acetyl-2,3-dihydro-5-hydroxynaphtho[2,3-b]furan-4,9-dione (0.5 g, 1.95 mmol) in chloroform (50 mL) is added 10 g of manganese dioxide (manufactured by Aldrich Corp., 90% manganese dioxide, for battery cell, <10 micron), and the resulting suspension is heated to reflux for 3 days. The mixture is cooled to room temperature, and then filtered. The filtrate is evaporated in vacuo and the residue is purified by silica gel column chromatography (eluent: chloroform) to give 2-acetyl-5-hydroxynaphtho[2,3-b]furan-4,9-dione (0.216 g, 44%) and 2-acetyl-2,3-dihydro-5-hydroxynaphtho[2,3-b]furan-4,9-dione (0.255 g, 51%). This method provides a method for preparing 2-acetyl-5-hydroxynaphtho[2,3-b]furan-4,9-dione at lower cost than Example 6.

EXAMPLE 8

Preparation of 2-(1-hydroxyethyl)-5-hydroxynaphtho[2,3-b]furan-4,9-dione

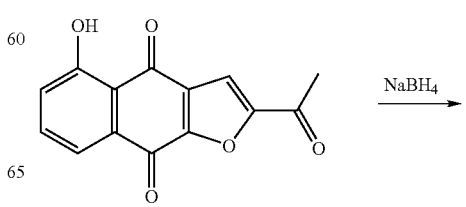

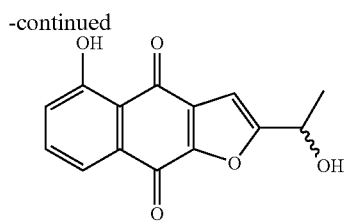

To a solution of 2-acetyl-5-hydroxynaphtho[2,3-b]furan-4,9-dione (694 mg, 2.73 mmol) obtained in Example 5 in chloroform (100 mL) and ethanol (25 mL) is added sodium borohydride (515 mg, 13.7 mmol) at 0° C. The mixture is stirred for 30 minutes, and then the reaction is quenched by adding 10% hydrochloric acid to the mixture. The aqueous layer is extracted with chloroform twice, and the extract is continuously washed with water and brine. The mixture is evaporated in vacuo and purified by silica gel column chromatography (eluent: chloroform) to give 2-(1-hydroxyethyl)-5-hydroxynaphtho[2,3-b]furan-4,9-dione (516 mg, 74%) as a racemic mixture of a yellow crystal.

Melting point: 148 to 149° C.

$^1$H-NMR (CDCl$_3$): δ 1.66 (3H, d, J=6.8 Hz), 2.31 (1H, brs), 5.05 (1H, m), 6.84 (1H, s), 7.27 (1H, dd, J=8.3, 1.0 Hz), 7.62 (1H, t, J=8.0 Hz), 7.75 (1H, dd, J=8.0, 0.9 Hz), 12.18 (1H, s).

The resulting racemic mixture can be separated by a chiral column chromatography in the following condition to give an enantiomer.

Column: SUMICHIRAL OA-4500 (4.6 mmϕ×250 mm)
Mobile phase: hexane/2-propanol/methanol=95:4:1
Detection: UV 254 nm
Flow: 1.0 mL/minutes
Temperature: room temperature (constant temperature around 25° C.)
Injection volume: 5 μL (0.1 mg/mL methanol)
Retention time: 30.8 and 34.4 minutes.

An enantiomer of 2-(1-hydroxyethyl)-5-hydroxynaphtho[2,3-b]furan-4,9-dione can be also separated each other by substituting "hexane/ethanol=95:5" for "hexane/2-propanol/methanol=95:4:1" for a mobile phase in the above condition, and in this case, the retention time is 24.9 and 27.4 minutes. A retention time of a naturally-derived 2-(1-hydroxyethyl)-5-hydroxynaphtho[2,3-b]furan-4,9-dione also referred to as β-isomer is 27.4 minutes in the chiral column chromatography in the same condition.

It has been found that a former elution is unnatural type (α-isomer) and a latter elution is natural type (β-isomer) considering each retention time of an enantiomer obtained by HPLC separation of synthetic 2-(1-hydroxyethyl)-5-hydroxynaphtho[2,3-b]furan-4,9-dione in the above condition using an optically-active column. Each property is shown in the following TABLE 1.

TABLE 1

|  | Unnatural Type (α-Isomer) | Natural Type (β-Isomer) |
|---|---|---|
| Purity | ≥99% | ≥99% |
| Melting point | 172-173.5° C. | 171-172° C. |

Antitumor activities and toxicities against normal cells are examined by using a racemate, α-isomer and β-isomer of 2-(1-hydroxyethyl)-5-hydroxynaphtho[2,3-b]furan-4,9-dione obtained in Example 8 as follows.

Experiment 1

Antitumor activities (1) Antitumor activity against PC-3 cells (Prostate cancer cells) (1)

PC-3 cells (manufactured by Department of Laboratory Products of Dainippon Pharm. Co. Ltd.) are preliminarily seeded in 35 mm petri dishes containing Dulbecco's modified Eagle medium (DMEM) containing 20% of fetal bovine serum (FBS) in a concentration of 1×10$^5$/ml. The resulting cells are incubated at 36° C. for 1 day under 5% CO$_2$, and cells are confirmed to be stuck at the bottom of the petri dishes. The resulting PC-3 cells are divided into three groups, to the first group of which is added (±)-2-(1-hydroxyethyl)-5-hydroxynaphtho[2,3-b]furan-4,9-dione (racemate) in concentrations of 0.5 mM, 0.05 mM and 0.005 mM, and to the second group of which is added adriamycin (Wakenyaku Co. Ltd.) as a control in concentrations of 0.5 mM, 0.05 mM and 0.005 mM. These groups are incubated at 36° C. for 3 days, and viable cells are counted and viability is calculated. The result is shown in TABLE 2.

TABLE 2

Comparison-1 of Anticancer Activity against PC-3 Cells

| Concentration (mM) | Racemate-treatment (Viability %) | Adriamycin-treatment (Viability %) |
|---|---|---|
| 0.5 | 0 | 0 |
| 0.05 | 0 | 0 |
| 0.005 | 50 | 42 |

(2) Antitumor activity against PC-3 cells (2)

PC-3 cells obtained in a similar manner in the above (1) are divided into three groups, to the first group of which is added (±)-2-(1-hydroxyethyl)-5-hydroxynaphtho[2,3-b]furan-4,9-dione (racemate) in concentrations of 0.5 mM, 0.05 mM, 0.005 mM and 0.0005 mM, to the second group of which is added an unnatural type 2-(1-hydroxyethyl)-5-hydroxynaphtho[2,3-b]furan-4,9-dione (α-isomer) in concentrations of 0.5 mM, 0.05 mM, 0.005 mM and 0.0005 mM, to the third group of which is added a natural type 2-(1-hydroxyethyl)-5-hydroxynaphtho[2,3-b]furan-4,9-dione (β-isomer) in concentrations of 0.5 mM, 0.05 mM, 0.005 mM and 0.0005 mM, and to the fourth group of which is added mitomycin as a control in concentrations of 0.5 mM, 0.05 mM, 0.005 mM and 0.0005 mM. These groups are incubated at 36° C. for 3 days, and viable cells are counted and viability is calculated. The result is shown in TABLE 3.

TABLE 3

Comparison-2 of Anticancer Activity against PC-3 Cells

| Concentration (mM) | Racemate-treatment (Viability %) | α-Isomer-treatment (Viability %) | β-Isomer-treatment (Viability %) | Mitomycin-treatment (Viability %) |
|---|---|---|---|---|
| 0.5 | 0 | 0 | 0 | 0 |
| 0.05 | 0 | 0 | 0 | 0 |
| 0.005 | 30 | 30 | 10 | 10 |
| 0.0005 | 50 | 60 | 40 | 40 |

(3) Antitumor activity against A-549 cells (Lung cancer cells)

Antitumor activity is examined on A-549 cells in a similar manner as in the above (2). The result is shown in TABLE 4.

TABLE 4

Comparison of Anticancer Activity against A-549 Cells

| Concentration (mM) | Racemate-treatment (Viability %) | α-Isomer-treatment (Viability %) | β-Isomer-treatment (Viability %) | Mitomycin-treatment (Viability %) |
|---|---|---|---|---|
| 0.5 | 0 | 0 | 0 | 0 |
| 0.05 | 10 | 10 | 10 | 0 |
| 0.005 | 50 | 40 | 30 | 10 |
| 0.0005 | 70 | 70 | 60 | 50 |

(4) Antitumor activity against MCF-7 cells (Breast cancer cells)

Antitumor activity is examined on MCF-7 cells in a similar manner as in the above (2). The result is shown in TABLE 5.

TABLE 5

Comparison of Anticancer Activity against MCF-7 Cells

| Concentration (mM) | Racemate-treatment (Viability %) | α-Isomer-treatment (Viability %) | β-Isomer-treatment (Viability %) | Mitomycin-treatment (Viability %) |
|---|---|---|---|---|
| 0.5 | 0 | 0 | 0 | 0 |
| 0.05 | 20 | 30 | 20 | 10 |
| 0.005 | 50 | 60 | 50 | 30 |
| 0.0005 | 90 | 90 | 70 | 60 |

Experiment 2

Cytotoxicity Assay for Human Skin Normal Cells (Cell System Fb cells), Human Hepatic Normal Cells (Cell Systems Hc Cells), Human Intestinal Normal Cells (Cell Systems IE Cells) and Human Lung Normal Cells (MRC-5)

Each human normal cells are preliminarily seeded in 35 mm petri dishes containing Dulbecco's modified Eagle medium (DMEM) containing 20% of fetal bovine serum (FBS) in a concentration of $1 \times 10^5$/ml. The resulting cells are incubated at 36° C. for 1 day under 5% $CO_2$, and cells are confirmed to be stuck at the bottom of the petri dishes. A racemate, α-isomer and β-isomer are each dissolved in DMSO to give solutions in concentrations of 0.5 mM, 0.05 mM, 0.005 mM and 0.0005 mM, 2 μL each of which are added to each cells. The resulting cells are incubated at 36° C. for 3 days, and viable cells are counted by using 0.25% trypan blue and viabilities are calculated. The results are shown in TABLEs 6 to 9. A commercially-available anticancer agent mitomycin is also examined as a control in the test against human skin normal cells, and the results are also shown in TABLE 6.

TABLE 6

Cytotoxicity against Human Skin Normal Cells

| Concentration (mM) | Racemate-treatment (Viability %) | α-Isomer-treatment (Viability %) | β-Isomer-treatment (Viability %) | Mitomycin-treatment (Viability %) |
|---|---|---|---|---|
| 0.5 | 20 | 30 | 10 | 0 |
| 0.05 | 50 | 40 | 20 | 0 |
| 0.005 | 80 | 70 | 50 | 30 |
| 0.0005 | 100 | 100 | 100 | 60 |

TABLE 7

Cytotoxicity against Human Hepatic Normal Cells

| Concentration (mM) | Racemate-treatment (Viability %) | α-Isomer-treatment (Viability %) | β-Isomer-treatment (Viability %) |
|---|---|---|---|
| 0.5 | 30 | 20 | 10 |
| 0.05 | 60 | 40 | 20 |
| 0.005 | 80 | 70 | 50 |
| 0.0005 | 100 | 100 | 100 |

TABLE 8

Cytotoxicity against Human Intestinal Normal Cells

| Concentration (mM) | Racemate-treatment (Viability %) | α-Isomer-treatment (Viability %) | β-Isomer-treatment (Viability %) |
|---|---|---|---|
| 0.5 | 40 | 40 | 30 |
| 0.05 | 60 | 60 | 50 |
| 0.005 | 80 | 80 | 70 |
| 0.0005 | 100 | 100 | 100 |

TABLE 9

Cytotoxicity against Human Lung Normal Cells

| Concentration (mM) | Racemate-treatment (Viability %) | α-Isomer-treatment (Viability %) | β-Isomer-treatment (Viability %) |
|---|---|---|---|
| 0.5 | 30 | 30 | 20 |
| 0.05 | 60 | 50 | 40 |
| 0.005 | 80 | 80 | 70 |
| 0.0005 | 100 | 100 | 100 |

An existing representative antitumor agent Mitomycin C shows very strong toxicity to normal cells as shown in TABLE 6.

The invention claimed is:

1. A method for preparing a compound of formula (III):

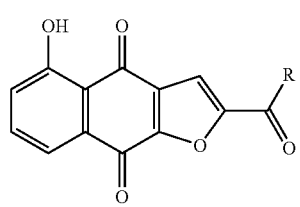

wherein R is $C_1$-$C_6$ alkyl,
comprising reacting a compound of formula (I):

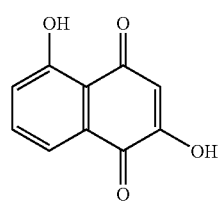

with a compound of formula (II):

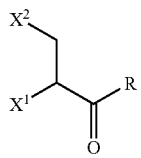
(II)

wherein R is the same as defined for the formula (III) above and $X^1$ and $X^2$ are each independently a halogen atom,
in the presence of at least one base selected from the group consisting of pyridine, DMAP (4-dimethylaminopyridine), quinoline, isoquinoline, triethylamine, diisopropylethylamine, DBU (1,8-diazabicyclo[5.4.0]undec-7-ene), DBN (1,5-diazabicyclo[4.3.0]non-5-ene), sodium hydroxide, potassium hydroxide, calcium hydroxide, sodium carbonate, and sodium bicarbonate.

2. A method for preparing a compound of formula (III):

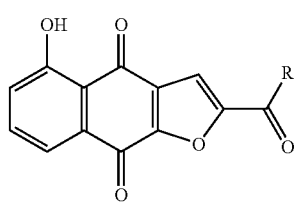
(III)

wherein R is $C_1$-$C_6$ alkyl,
comprising reacting a compound of formula (I):

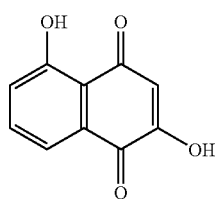
(I)

with a compound of formula (II):

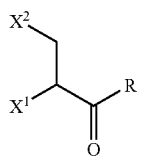
(II)

wherein R is the same as defined for the formula (III) above and $X^1$ and $X^2$ are each independently a halogen atom,
in the presence of at least one base selected from the group consisting of pyridine, DMAP (4-dimethylaminopyridine), quinoline, isoquinoline, triethylamine, diisopropylethylamine, DBU (1,8-diazabicyclo[5.4.0]undec-7-ene), DBN (1,5-diazabicyclo[4.3.0]non-5-ene), sodium hydroxide, potassium hydroxide, calcium hydroxide, sodium carbonate, and sodium bicarbonate to give a compound of formula (VII):

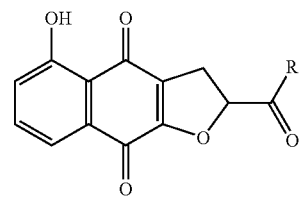
(VII)

wherein R is the same as defined for the formula (III) above, followed by oxidizing the resulting compound (VII) with at least one oxidizing agent selected from the group consisting of manganese dioxide, potassium permanganate, $CrO_3$, $Na_2Cr_2O_7$, PbO, $PbO_2$, Pb(OCOCH$_3$)$_4$, HgO, AgO, $Ag_2O$, $AgNO_3$, $CuCl_2$, $FeCl_3$, $Cl_2$, $Br_2$, $I_2$, NaClO, $KBrO_3$, $KIO_4$, oxygen, ozone, $H_2O_2$, $Na_2O_2$, $(C_6H_5CO)_2O_2$, $CH_3CO_3H$, $C_6H_5CO_3H$, and $K_2S_2O_8$.

3. The method of claim 2, wherein the oxidizing agent is manganese dioxide.

4. The method of claim 1, wherein the R is methyl.

5. The method of claim 1, wherein the $X^1$ and the $X^2$ are each bromine atom.

6. The method of claim 1, wherein the base is DBU.

7. A method for preparing a compound of formula (IV):

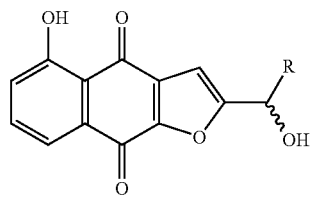
(IV)

wherein R is $C_1$-$C_6$ alkyl and a wavy line refers to a racemate, comprising reacting a compound of formula (I):

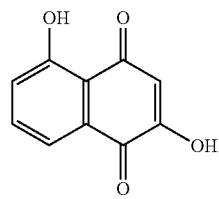
(I)

with a compound of formula (II):

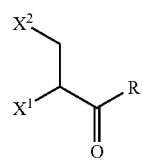
(II)

wherein R is the same as defined for the formula (IV) above and $X^1$ and $X^2$ are each independently a halogen atom,
in the presence of at least one base selected from the group consisting of pyridine, DMAP (4-dimethylaminopyridine), quinoline, isoquinoline, triethylamine, diisopropylethylamine, DBU (1,8-diazabicyclo[5.4.0]undec-7-ene), DBN (1,5-diazabicyclo[4.3.0]non-5-ene), sodium hydroxide, potassium hydroxide, calcium hydroxide, sodium carbonate, and sodium bicarbonate to give a compound of formula (III):

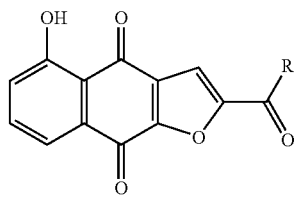
(III)

wherein R is the same as defined for the formula (IV) above, followed by reducing the resulting compound (III) with at least one reducing agent selected from the group consisting of sodium borohydride (NaBH$_4$), potassium borohydride, lithium borohydride, sodium aluminum hydride, potassium aluminum hydride, lithium aluminum hydride, zinc borohydride, sodium triacetoxyborohydride, pyridine/borane sodium cyanoborohydride sodium amalgam H$_2$/Pd, H$_2$/Pd-C, H$_2$/Pt, H$_2$/PtO$_2$, H$_2$/Rh, and H$_2$/Raney nickel.

8. A method for preparing a compound of formula (IV):

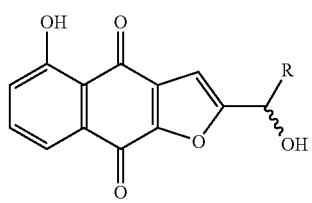
(IV)

wherein R is C$_1$-C$_6$ alkyl and a wavy line refers to a racemate, comprising reacting a compound of formula (I):

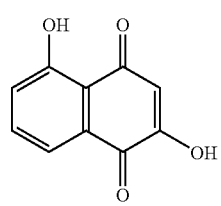
(I)

with a compound of formula (II):

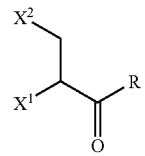
(II)

wherein R is the same as defined for the formula (IV) above and X$^1$ and X$^2$ are each independently a halogen atom, in the presence of at least one base selected from the group consisting of pyridine, DMAP (4-dimethylaminopyridine), quinoline, isoquinoline, triethylamine, diisopropylethylamine, DBU (1,8-diazabicyclo[5.4.0]undec-7-ene), DBN (1,5-diazabicyclo[4.3.0]non-5-ene), sodium hydroxide, potassium hydroxide, calcium hydroxide, sodium carbonate, and sodium bicarbonate to give a compound of formula (VII):

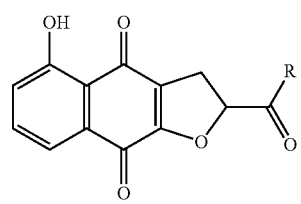
(VII)

wherein R is the same as defined for the formula (IV) above,
followed by oxidizing the resulting compound (VII) with at least one oxidizing agent selected from the group consisting of manganese dioxide, potassium permanagnate, CrO$_3$, Na$_2$Cr$_2$O$_7$, PbO, PbO, Pb(OCOCH$_3$)$_4$, HgO, AgO, Ag$_2$O, AgNO$_3$, CuCl$_2$, FeCl$_3$, Cl$_2$, Br$_2$, I$_2$, NaClO, KBrO$_3$, KIO$_4$, oxygen, ozone, H$_2$O$_2$, Na$_2$O$_2$, (C$_6$H$_5$CO)$_2$O$_2$, CH$_3$CO$_3$H, C$_6$H$_5$CO$_3$H, and K$_2$S$_2$O$_8$ to give a compound of formula (III):

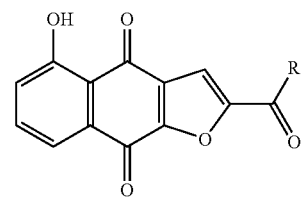
(III)

wherein R is the same as defined for the formula (IV) above, and reducing the resulting compound (III) with at least one reducing agent selected from the group consisting of sodium borohydride (NaBH$_4$), potassium borohydride, lithium borohydride, sodium aluminum hydride, potassium aluminum hydride, lithium aluminum hydride, zinc borohydride, sodium triacetoxyborohydride, pyridine/borane, sodium cyanoborohydride, sodium amalgam, H$_2$/Pd, H$_2$/Pd—C, H$_2$/Pt, H$_2$/PtO, H$_2$/Rh and H$_2$/Raney nickel.

9. The method of claim 7, wherein the reducing agent is NaBH$_4$.

10. The method of claim 7, which further comprises a step of resolving a compound of the formula (IV):

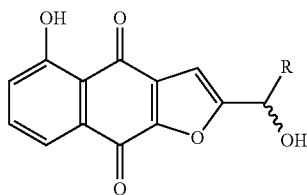
(IV)

wherein R is the same as defined in claim 7 above and a wavy line refers to a racemate, by a HPLC process to give α- and β-isomers of 2-(1-hydroxyethyl)-5-hydroxynaphtho[2,3-b]furan-4,9-dione.

11. The method of claim 1, which further comprises a step of reacting a dimethylamine dissolved in a solvent with a compound of formula (V):

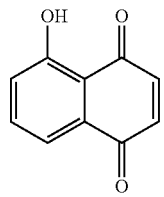

(V)

to give a compound of formula (VI):

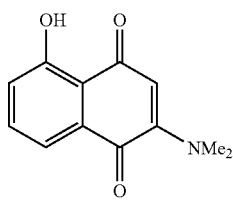

(VI)

and a step of reacting the resulting compound of the formula (VI) with 5 to 15% (w/w) of an aqueous acid solution to give a compound of the formula (I).

12. The method of claim 11 wherein the aqueous acid solution is an aqueous hydrochloric acid solution.

13. The method of claim 2, wherein the R is methyl.

14. The method of claim 2, wherein the $X^1$ and the $X^2$ are each bromine atom.

15. The method of claim 2, wherein the base is DBU.

16. The method of claim 8, wherein the reducing agent is NaBH$_4$.

17. The method of claim 8, which further comprises a step of resolving the compound of formula (IV):

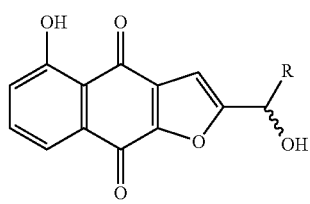

(IV)

wherein R is the same as defined in claim 8 above and a wavy line refers to a racemate, by a HPLC process to give α- and β-isomers of 2-(1-hydroxyethyl)-5- hydroxynaphtho[2,3-b]furan-4,9-dione.

18. The method of claim 2, which further comprises a step of reacting a dimethylamine dissolved in a solvent with a compound of formula (V):

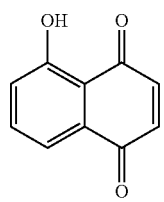

(V)

to give a compound of formula (VI):

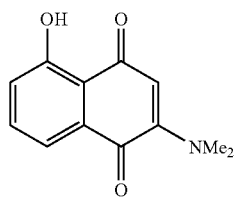

(VI)

and a step of reacting the resulting compound of the formula (VI) with 5 to 15% (w/w) of an aqueous acid solution to give a compound of the formula (I).

19. The method of claim 7, which further comprises a step of reacting a dimethylamine dissolved in a solvent with a compound of formula (V):

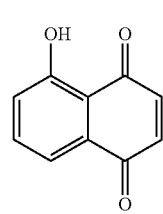

(V)

to give a compound of formula (VI):

(VI)

and a step of reacting the resulting compound of the formula (VI) with 5 to 15% (w/w) of an aqueous acid solution to give a compound of the formula (I).

20. The method of claim 8, which further comprises a step of reacting a dimethylamine dissolved in a solvent with a compound of formula (V):

(V)

to give a compound of formula (VI):

(VI)

and a step of reacting the resulting compound of the formula (VI) with 5 to 15% (w/w) of an aqueous acid solution to give a compound of the formula (I).

* * * * *

UNITED STATES PATENT AND TRADEMARK OFFICE
CERTIFICATE OF CORRECTION

| | | |
|---|---|---|
| PATENT NO. | : 7,910,752 B2 | Page 1 of 1 |
| APPLICATION NO. | : 11/885216 | |
| DATED | : March 22, 2011 | |
| INVENTOR(S) | : Tokuda et al. | |

It is certified that error appears in the above-identified patent and that said Letters Patent is hereby corrected as shown below:

Column 20, line 24 (claim 8): "permanagnate" should read -- permanganate --.
Column 20, line 25 (claim 8): "PbO" should read -- $PbO_2$ --.
Column 20, line 49 (claim 8): "$H_2$/PtO" should read -- $H_2/PtO_2$ --.
Column 20, line 50 (claim 8): "$H_2$/Rh" should read -- $H_2$/Rh, --.

Signed and Sealed this

Second Day of August, 2011

David J. Kappos
*Director of the United States Patent and Trademark Office*